United States Patent [19]

Brenner et al.

[11] Patent Number: 4,988,510

[45] Date of Patent: Jan. 29, 1991

[54] INSECT CONTROL SYSTEM

[75] Inventors: Richard J. Brenner; Richard S. Patterson, both of Gainesville, Fla.; Roger R. Pierce, Cashiers, N.C.; Marvin H. Hult, Peoria, Ill.

[73] Assignee: The United States of America as represented by the Secretary of Agriculture, Washington, D.C.

[21] Appl. No.: 373,310

[22] Filed: Jun. 29, 1989

[51] Int. Cl.$^5$ .............................................. A01N 25/00
[52] U.S. Cl. ..................................... 424/84; 424/408; 424/409; 426/1
[58] Field of Search ................. 424/84, 405, 410, 411, 424/412, 418, 419, 420, 408, 409

[56] References Cited

U.S. PATENT DOCUMENTS

| | | | |
|---|---|---|---|
| 3,091,567 | 5/1963 | Wurtzbung | 167/42 |
| 4,470,979 | 11/1984 | Van Gestel | 514/166 |
| 4,807,391 | 2/1989 | Bokiau | 43/131 |
| 4,823,506 | 4/1989 | Demarest et al. | 43/131 |

OTHER PUBLICATIONS

Victor E. Adler, 1985, A Highly Effective Attractant for the Brownbanded Cockroach, J. Environ, Sci. Health A 20(8), 839–844.

Richard J. Brenner, "Focality and Mobility of Some Peridomestic Cockroaches in Florida (Dictyoptera: Blattaria)," Ann. Entomol. Soc. Am. 81(4): 581–592 (1988).

Richard J. Brenner et al., "Laboratory Feeding Activity and Bait Preferences of Four Species of Cockroaches (Orthoptera: Blattaria)," J. Econ. Entomol. 82(1): 159–162 (1989).

Advertising Brochure, "Its Works, The Inside Story," Residex Corporation, 3029 Fairfield Avenue, Bridgeport, CT 06605.

Victor E. Adler, "A Highly Effective Attractant for the Brownbanded Cockroach (Orthoptera: Blattellidae)," J. Environ. Sci. Hlth. A20(8): 839–844, (1985).

*Primary Examiner*—Douglas W. Robinson
*Assistant Examiner*—Russell Travers
*Attorney, Agent, or Firm*—M. Howard Silverstein; John D. Fado; Curtis P. Ribando

[57] ABSTRACT

A packaged bait system for the control of insects, especially cockroaches and other orthopterous insects, comprising an insecticidal food bait composition housed in a bait block holder that allows for easy placement in locations where the probability of encounter by the target insect is high and that makes the bait readily accessible to the target insect. The toxic bait comprises corn distiller's grain, a humectant, an insecticide and a gel former to yield a deformable hydrophilic gel matrix subsequent to hydration.

12 Claims, 1 Drawing Sheet

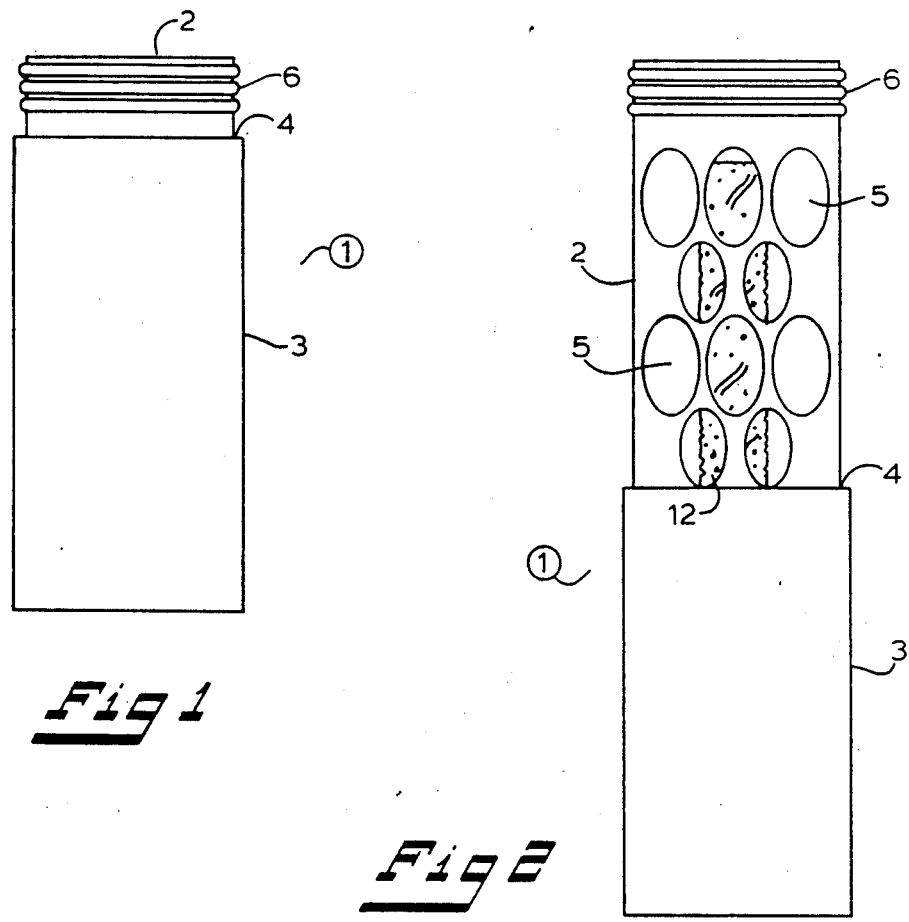
*Fig 1*
*Fig 2*
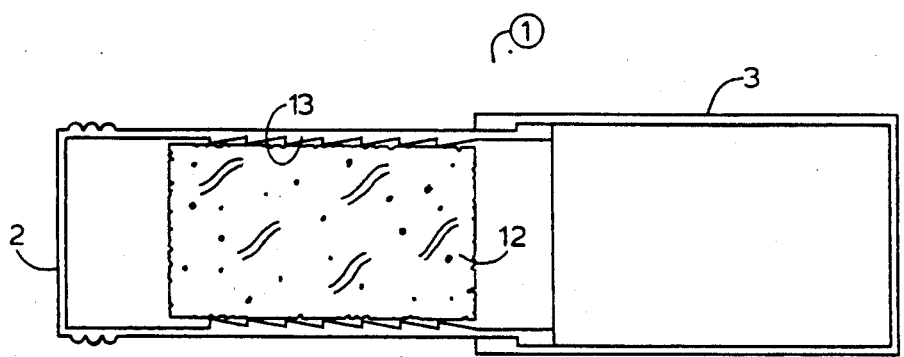
*Fig 3*
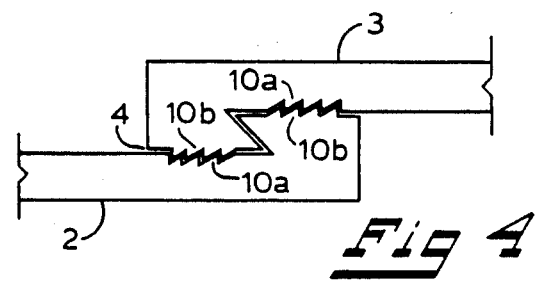
*Fig 4*

INSECT CONTROL SYSTEM

BACKGROUND OF THE INVENTION

1. Field of the Invention

Cockroaches are primarily tropical insects but some species have become widely disseminated through commercial activities and are now cosmopolitan. The domestic species are omnivorous but are especially attracted to starchy or sweetened matter of various kinds; they also attack food, paper, clothing, books, shoes, bones, and dead insects. They are the only orthopterous insects that are involved in the contamination of food. Of the many species of cockroaches, house inhabitors include American (*Periplaneta americana*), oriental (*Blatta orientalis*), Australian (*P. australasiae*), German (*Blattella germanica*), brownbanded [*Supella longipalpa* (F.)], smokybrown [*P. fuliginosa* (Serville)], and Florida woods [*Eurycotis floridana* (Walker)] cockroaches. They prefer secluded, warm, damp places and, at night or on dark days, they sample filth and foods and impart to infested areas an unpleasant odor.

This invention relates to a system designed for use in insect control programs, especially those designed to control cockroaches.

2. Description of the Prior Art

The dried mash from a distillery was reported by Adler [J. Environ. Sci. Hlth. A20:839–844 (1985) to be specifically attractive for the brownbanded cockroch, *Supella longipalp* (F.), but is failed to attract American cockroaches, *Periplaneta americana* (L.). In contrast, Brenner et al. [Ann. Entomol. Soc. Am. 81:581–592 (1988); J. Med. Entomol. 25:489–592 (1988); J. Econ. Entomol. 82:159–162 (1989)] reported that distiller's dried grains with solubles (DDGS, Agricultural Energy Corp., Franklin, KY) was attractive to 15 species of cockroaches including American cockroaches. Furthermore, the DDGS is advantageously unattractive to nontarget mammals, in contrast to other baits such as pieces of fruit, bread, and beer [Jackson et al., Am. J. Trop. Med. Hyg. 4:141–146 (1955), Ohio J. Sci. 61:220–226 (1961); Reierson et al., Pest Control 45: 40, 42–44 (1977); Fleet et al., Environ. Entomol. 7:807–814 (1978)] or dry cat food [Appel et al., Environ. Entomol. 14:669–673 (1985)] which are attractive to mammals as well as cockroaches.

A number of food attractants have been formulated with toxicants and aqueous gel binders to provide toxic paste baits for cockroaches. For example, Doi et al. [Chem. Abst. 107:129156n (1987)] controlled cockroaches with a paste containing boric acid, potato starch, corn starch, rice bran, molasses, water, and dye; Barson [Chem. Abst. 97:87017k (1982)] used a mixture of boric acid plus porridge oats and iodofenphos gel; and Peeters [Chem. Abst. 84: 131508d (1976)] combined bakery wastes, boric acid, and water. Similarly, the proprietary roach bait station sold under the trademark, "It Works" (Bridgeport, CT) is advertised as containing boric acid, an attractant, and a humectant.

SUMMARY OF THE INVENTION

We have now invented a packaged insect bait which is especially effective in controlling cockroaches, i.e., members of the Blattaria, a suborder of orthopterous insects. The bait system for cockroach control comprises a food bait composition housed in a bait block holder. The bait composition comprises an attractant, one or more humectants, and an insecticide formulated together in a deformable hydrophilic gel matrix. The bait is optionally enveloped in a water-impermeable, insect-edible coating or film. The bait composition is also useful in controlling other orthopterous insects, such as crickets and grasshoppers, as well as insect species of other orders, including fireants (order: Hymenoptera; family: Formicidae)

In accordance with this discovery, it is an object of the invention to provide an insect bait station that offers a potential alternative to frequent blanket application of pesticides, thus reducing the costs and risks of insecticide contamination.

It is also an object of the invention to provide an insect food bait that contains a nonleaching insecticide and that does not attract mammals, thus further reducing the risks of environmental contamination and nontarget injury.

Another object of this invention is to provide an insect food bait which is attractive to target insects under microclimate conditions when the insects are most in need of food and moisture.

It is a further object of the invention to provide an insect bait that is widely attractive to various species of the target insect.

Still another object of the invention is to provide an insect bait in a form that has a long shelf life and that is easily handled.

Yet another object of the invention is to produce a bait block holder that keeps the bait fresh until needed, that reduces risks of mishandling, that allows for easy placement in locations where the probability of encounter by the target insect is high, that makes the bait readily accessible to the target insect, and that allows for easy replenishment of the bait block as needed.

It is also an object of the invention to design an insect bait system that can be used in moist environments such as sewer systems.

Other objects and advantages of this invention will become readily apparent from the ensuing description.

BRIEF DESCRIPTION OF THE DRAWINGS

FIGS. 1–4 illustrate a preferred embodiment of the invention.

FIG. 1 is a perspective view of the bait holder in the closed configuration prior to use.

FIG. 2 is a perspective view of the bait holder in the open configuration ready for use.

FIG. 3 is a cross-sectional view of the holder in the open configuration with a bait block in place.

FIG. 4 is a detailed view of the locking mechanism for maintaining the bait holder in the open configuration.

DETAILED DESCRIPTION OF THE INVENTION

The component for use in the bait of this invention for attracting a broad spectrum of cockroach species and other insects is corn distiller's dried grains with solubles obtained from nonbeverage alcohol production. This material, hereafter referred to as C-DDGS, is the residue remaining after distilling a corn fermentate. Unlike similar products from alcoholic beverage distilleries utilizing grains other than corn, the C-DDGS is highly effective as a bait ingredient for most species of peridomestic cockroaches but is not attractive to mammals such as dogs, cats, raccoons, and wood rats.

The humectant materials contemplated for use in the invention comprise any hygroscopic substance or combination of substances that draw moisture from the air, allowing the bait formulation to remain pliable and relatively moist. Sugars, glycerol, and other polyhydroxy alcohols are exemplary of the substances useful for this purpose. Some humectants, such as sugars, provide the further advantage of enhancing the attractiveness of the bait composition.

The preferred class of insecticides for use herein are the microencapsulated insecticides characterized by the property of being semipermeable in the absence of free water but becoming impermeable in a wet environment. This property prevents the loss of insecticide by leaching, but it permits release when the capsules are physically crushed, as during the act of chewing by cockroaches. By using microencapsulated insecticides, substantially the only release of toxicant in the cockroach habitat occurs within the alimentary tracts of the target organisms. Of course, if the threat of leaching it not a factor, other conventional insecticides, such as those which are not encapsulated, can be used.

The gel formers for use herein provide an elastic, cohesive matrix that holds the DDGS together in combination with the other bait ingredients. Gum xanthan is especially suitable for this purpose for the reason that is i hydrophilic and serves as a humectant. It is anticipated that any other gelling agent that is not repulsive to roaches can also be used, provided that the resultant matrix freely releases the aromatic elements of the C-DDGS at temperatures of high cockroach feeding activity. Guar gum is such an alternative gel.

Preservatives are optional in the baits of the invention but are recommended for baits to be used in very humid or moist conditions. Illustrative of these are methyl paraben (p-hydroxybenoic acid methyl ester) and propyl paraben (n-propyl p-hydroxybenzoate), each used at concentrations of approximately 0.01%. Other known fungistats would also be effective in increasing the longevity of the bait and retarding mold growth.

Each component should be present in an effective amount. The expression "effective amount" is defined herein to mean that amount which is necessary to achieve the intended result of the component in question. For example, an effective amount of the insecticide is that level, or concentration, which will kill significantly more target insects when the bait is consumed than when an equivalent amount of bait is consumed without the insecticide present. Likewise, an effective amount of attractant is that which will attract more target insects to the bait than a control bait without the attractant. On a dry weight basis, the components of the bait compositions will typically be present in about the following amounts: 45–65% C-DDGS, 30–45% humectants, 6–10% gel former, 0.2–5% active ingredient (in insecticide), and 0–2% preservative.

To prepare the bait, the gel former is dispersed in water either before or after addition of the other components of the bait formulation. The amount of water should be sufficient to hydrate the gel former to the extent that the mixture is converted to a shapable matrix. In a preferred embodiment, the amount of water is selected to yield a matrix having a rubbery consistency which can be shaped into a deformable mass without the need for excessive dewatering. Optionally the matrix is dried to a water content of about 10% by any conventional method as known in the art.

The water-impermeable, insect-edible coating is intended to facilitate handling and increase shelf life of the bait, especially when it is not prepackaged in the bait holder described below. A film of paraffin is suitable for this purpose, but it is anticipated that other materials can also be used. Coating with paraffin can be accomplished either by wrapping the bait block with paraffin film or by dipping the bait in hot liquid paraffin. The preferred paraffin affords the advantage that it is readily eaten by cockroaches. Thus it need not be removed before use; simple scoring or tearing of the surface will expose the bait and release aromatic components.

Referring to FIGS. 1 and 2, the bait holder of this invention comprises a capsule 1 having a telescoping, apertured, inner portion 2, and a protective, substantially impervious outer portion 3. Portions 2 and 3 may be constructed of plastic, cardboard, or other comparatively rigid material substantially free of substances which would repel insects. When the capsule is closed (as for storage and shipment), portions 2 and 3 are held together by means of a suitable shrink wrap or else a sealing tape (not shown) over joint 4. At the time of use, the two portions are telescoped apart to expose apertures 5. Ribbing 6 facilitates grasping of inner portion 2. The portions are locked in the open configuration as best shown in FIGS. 2 and 3 by means of frictional engagement of opposing denticulated surfaces 10a and 10b shown in detail in FIG. 4. Alternatively, a tab and groove, or other locking mechanism as known in the art, could be employed. Bait block 12 is held in place within inner portion 2 by means of serrations 13 integral with the interior surface of the inner portion. Apertures 5 are sized to permit the target insects access to the bait when the holder is in the open configuration. The apertures also allow visual observation of the bait supply to determine when replenishment is needed.

The capsule 1 may assume a variety of shapes but will usually have a circular or rectangular cross section. In a preferred embodiment of the invention, a bait holder for use in the control of roaches would be dimensioned as follows: cross section, 3.8 cm; length (closed), 8.9 cm; and length (open), 14 cm. The apertures 5 would be elliptical openings ranging in size from 1×1.25 cm to about 1.25×2 cm.

The elasticity of the bait is important to its use in combination with the design of the bait holder described above. By initially sizing the bait blocks slightly larger than the internal space defined by the serrated surface of inner portion 2, the deformable bait will become compressed when inserted into the bait holder and thereby rigidly engaged by the serrations 13.

At the time of use, the open bait holder 1 is placed in attics, tree holes, wall voids, block walls, wood piles, and other habitats indicated by the behavior of peridomestic cockroaches. Analysis of microclimate parameters in attics, wall voids, and wood piles indicates that temperatures may reach extremes greater than 40° C., causing dramatic shifts in the drying power of air and predisposign cockroaches to search for adequate food and moisture sources. The ingredients of the invention bait have been selected to enhance attractiveness under these extreme conditions.

Because the bait material of this invention is not damaged by moisture, it is envisioned that the bait system can be used in moist environments such as sewer systems by adaptation of the bait holder. For example, the bait system could be floated above anchorage points or, alternatively, bait stations could be adhered to the side walls of sewer access points.

This novel invention finds application for typical orthopterous insects (crickets and grasshoppers), principally cockroaches. Without limitation thereto, exemplary cockroaches include *Blattella asahinai* Mizukubo, *Cariblatta lutea lutea* (Saussure and Zehntner), *Eurycotis floridana* (Walker), *Ischnoptera deropeltiformis* (Brunner), *Latiblattella rehni* Hebard, *Panchlora nivea* (L.), *Parcoblatta caudelli* Hebard, *Parcoblatta divisa* (Saussure and Zehntner), *Parcoblatta fulvescens* (Saussure and Zehntner), *Parcoblatta lata* (Brunner), *Periplaneta americana* (L.), *Periplaneta australasiae* (F.), *Periplaneta brunnea* Burmeister, *Periplaneta fuliginosa* (Serville), and *Pycnoscelus surinamensis* (L.). Fireants are also readily controlled by the bait composition.

The following examples are intended only to further illustrate the invention and are not intended to limit the scope of the invention which is defined by the claims.

EXAMPLE 1

Response of Cockroaches to Bait Ingredients

A bait formulation without the microencapsulated insecticide, was prepared in the following manner. C-DDGS (250) g), gum xanthan (37.5 g), and sucrose (150 g) were thoroughly mixed dry. Water (300 ml) containing glycerol (25 ml) was added to the dry ingredients, and mixing was continued until a rubbery consistency was achieved. The mixture was transferred to a sheet of waxed paper, covered with another sheet of waxed paper, and rolled to a thickness of about ⅛ in. The covering sheet of waxed paper was removed, and the resulting slab of bait was dried for 48 hr at 300° C. The bait was then transferred from the waxed paper to a screen, dried for an additional 4 hr in a stream of moving air at room temperature, and allowed to stand for 48 hr at room temperature. The slab was then cut into blocks.

To evaluate cockroach response, bait was placed inside condiment cups, and aluminum mosquito screening was pressed over the bait so that cockroaches could sense and touch it but not consume it entirely. Activity data were obtained in research attics (located in Gainesville, FL) by using electronic sensors (capacitive sensors) positioned directly above cockroach bait stations containing the experimental bait. Sensors were monitored every 62 millisec, and the sensors were triggered whenever a cockroach passed between the bait and the sensor. Once triggered, the data logger recorded the event and its duration. An "event" is defined as one on-off cycling of a sensor, signifying a visit by a cockroach.

The impact of temperature on cockroach activity is reported in Table I. As temperature rose, cockroaches spent an increasing amount of time on the bait. These data support the idea that the bait, remaining somewhat more moist than the air, tends to attract and hold cockroaches when under stress. Cockroach activity by hour of day is reported in Table II. The data on visit duration are useful for recognizing when a lethal dose is likely to be consumed. Activity as a function of saturation deficit (SD) is reported in Table III, where "saturation deficit" is defined as the amount of moisture needed to bring air to saturation, expressed as pounds per square inch at atmospheric pressure (psia). These data demonstrate that cockroaches, being at risk of dehydration at higher SD, are drawn to the bait as SD increases. Taken collectively, these data demonstrate that cockroach activity on the invention bait increases as temperature and SD increase. When cockroaches are under minimal environmental stress, their activity is changeable. However, with increasing environmental stress (such as increasing temperature which increases metabolism, requiring more food, and increasing SD which increases rate of water loss), cockroaches are attracted to the bait, which provides both food and a relatively more moist environment.

EXAMPLE 2

Preparation of Bait Containing Insecticide

A bait formulation was prepared in accordance with the procedure described in Example 1 except that 19.1 g (calculated to provide 0.5% active ingredient in the final bait mixture) of the microencapsulated insecticide, "Dursban ME" (Dow Chemical), was included in the water-glycerol solution, and drying procedures were altered to avoid using an oven and to avoid leaving the bait under an operating fume hood unattended. The end result, as in Example 1, was a physically manageable slab of bait that was cut into squares for use.

EXAMPLE 3

Cricket Control

A bait formulation containing the microencapsulated insecticide, "Dursban ME", prepared as described in Example 2 was cut into blocks

TABLE I

| Temperature[a] (°C.) | No. of visits | Average activity[b] (seconds) |
| --- | --- | --- |
| 4 | 0.0 | 0.0 |
| 5 | 0.0 | 0.0 |
| 6 | 0.0 | 0.0 |
| 7 | 0.0 | 0.0 |
| 8 | 0.0 | 0.0 |
| 9 | 0.0 | 0.0 |
| 10 | 8.0 | 0.1 |
| 11 | 78.0 | 0.1 |
| 12 | 175.0 | 0.1 |
| 13 | 591.0 | 0.2 |
| 14 | 1027.0 | 0.2 |
| 15 | 1629.0 | 0.2 |
| 16 | 1943.0 | 0.2 |
| 17 | 1773.0 | 0.3 |
| 18 | 2400.0 | 0.3 |
| 19 | 2920.0 | 0.4 |
| 20 | 4173.0 | 0.2 |
| 21 | 3705.0 | 0.3 |
| 22 | 5867.0 | 0.2 |
| 23 | 4275.0 | 0.3 |
| 24 | 2023.0 | 0.3 |
| 25 | 2197.0 | 0.3 |
| 26 | 1489.0 | 0.5 |
| 27 | 355.0 | 2.4 |
| 28 | 41.0 | 6.2 |
| 29 | 55.0 | 7.2 |
| 30 | 215.0 | 4.1 |

[a] Each temperature shown actually represents a range of temperatures; e.g., 4 = 4.0–4.9, 5 = 5.0–5.9, etc.
[b] Data are corrected for irregular number of times that a given temperature may occur. In this manner, the data accurately reflect activity.

TABLE II

| Hour of day | No. of visits | Cumulative time (seconds) | Average visit duration (seconds) |
| --- | --- | --- | --- |
| 0 | 2800 | 101721.6 | 36.3 |
| 1 | 3468 | 96916.7 | 27.9 |
| 2 | 2688 | 109604.8 | 40.8 |
| 3 | 2590 | 101182.9 | 39.1 |

TABLE II-continued

| Hour of day | No. of visits | Cumulative time (seconds) | Average visit duration (seconds) |
|---|---|---|---|
| 4 | 3050 | 91733.2 | 30.1 |
| 5 | 1688 | 78499.6 | 46.5 |
| 6 | 889 | 54464.3 | 61.3 |
| 7 | 289 | 51154.6 | 177.0 |
| 8 | 138 | 39017.8 | 282.7 |
| 9 | 214 | 41570.2 | 194.3 |
| 10 | 245 | 42732.0 | 174.4 |
| 11 | 291 | 37720.3 | 129.6 |
| 12 | 290 | 48994.6 | 168.9 |
| 13 | 303 | 51760.3 | 170.8 |
| 14 | 522 | 51323.1 | 98.3 |
| 15 | 467 | 60561.7 | 129.7 |
| 16 | 983 | 59411.0 | 60.4 |
| 17 | 1473 | 74209.5 | 50.4 |
| 18 | 5467 | 88171.6 | 16.1 |
| 19 | 5053 | 100898.7 | 20.0 |
| 20 | 4257 | 97531.2 | 22.9 |
| 21 | 3457 | 88967.7 | 25.7 |
| 22 | 3309 | 96638.0 | 29.2 |
| 23 | 3004 | 103898.8 | 34.6 |

TABLE III

| Saturation deficit | Average activity[a] (seconds) |
|---|---|
| 0.01 | 0.7 |
| 0.02 | 0.1 |
| 0.03 | 0.0 |
| 0.04 | 0.1 |
| 0.05 | 0.1 |
| 0.06 | 0.0 |
| 0.07 | 1.1 |
| 0.08 | 0.5 |
| 0.09 | 0.4 |
| 0.10 | 1.2 |
| 0.11 | 0.5 |
| 0.12 | 0.0 |
| 0.13 | 4.1 |
| 0.14 | 1.9 |
| 0.15 | 0.0 |
| 0.16 | 10.0 |
| 0.17 | 0.1 |
| 0.18 | 9.4 |
| 0.19 | 0.0 |
| 0.20 | 48.4 |
| 0.21 | 21.5 |
| 0.22 | 0.1 |
| 0.23 | 0.0 |
| 0.24 | 0.0 |
| 0.25 | 0.0 |
| 0.26 | 0.0 |
| 0.27 | 0.0 |

[a] Data are corrected for nonuniform occurrence of SD.

approximately 1-cm square and 0.5-cm thick. The bait was place din containers with a water source, and 25 crickets were added. The trial was run in duplicate against a check in which "Purina Laboratory Rat Chow" was substituted for the bait formulation of the invention. The results are reported in Table IV below.

TABLE IV

| | Cricket Trial | | |
|---|---|---|---|
| | Percent Mortality | | |
| Hours | Replicate A | Replicate B | Check |
| 24 | 80 | 80 | 0 |
| 48 | 90 | 90 | 10 |
| 72 | 100 | 100 | 20 |

EXAMPLE 3

Fireant Control

The procedure of Example 3 was repeated except that fireants were substituted for the crickets, and crickets were used as the food source for the check instead of the "Purina Laboratory Rat Chow". In both treatment replicates, there was 100% mortality of the fireants after 24 hrs as compared to 0% mortality for the check.

It is understood that the foregoing detailed description is given merely by way of illustration and that modification and variations may be made therein without departing from the spirit and scope of the invention.

We claim:

1. A toxic insect bait for controlling a target insect comprising a deformable hydrophilic gel matrix comprising an amount of corn distiller's dried grain with soluble effective to attract said insect, a humectant, an insecticide which is toxic to said target insect, and a gel former in an amount effective to yield said deformable hydrophilic gel matrix subsequent to hydration.

2. A bait as described in claim 1 wherein said gel former is xanthan gum.

3. A bait as described in claim 1 wherein said humectant comprises a mixture of sucrose and glycerol.

4. A bait as described in claim 1 wherein said insecticide is encapsulated in microcapsules which are characterized by the property of being semipermeable in the absence of free water and substantially impermeable in the presence of free water.

5. A bait as described in claim 1 and further comprising an effective amount of a fungistat as a preservative.

6. A method of controlling a target insect comprising introducing to the locus of said insect a bait comprising a deformable hydrophilic gel matrix comprising an amount of corn distiller's dried grain with solubles effective to attract said insect, a humectant, an insecticide which is toxic to said target insect, and a gel former in an amount effective to yield said deformable hydrophilic gel matrix subsequent to hydration.

7. A method as described in claim 6 wherein said target insect is a cockroach.

8. A method as described in claim 6 wherein said gel former is xanthan gum.

9. A method as described in claim 6 wherein said humectant comprises a mixture of sucrose and glycerol.

10. A method as described in claim 6 wherein said insecticide is encapsulated in microcapsules which are characterized by the property of being semipermeable in the absence of free water and substantially impermeable in the presence of free water.

11. A method as described in claim 6 and further comprising an effective amount of a fungistat as a preservative.

12. A method as described in claim 6 wherein said target insect is a fireant.

* * * * *

UNITED STATES PATENT AND TRADEMARK OFFICE
CERTIFICATE OF CORRECTION

PATENT NO.   :   4,988,510

DATED        :   January 29, 1991

INVENTOR(S)  :   Richard J. Brenner and Richard S. Patterson

It is certified that error appears in the above-identified patent and that said Letters Patent is hereby corrected as shown below:

Title page, column 1, delete inventors Roger R. Pierce and Marvin H. Hult .
Column 1, line 30, delete "*longipalp*" and insert -- *longipalpa* -- ;
Column 1, line 30, delete "is" and insert -- it -- .
Column 3, lines 26-27, delete "is i" and insert -- it is -- .
Column 4, line 60, delete "predisposign" and insert -- predisposing -- .
Column 5, line 33, delete "300° C." and insert -- 33° C. -- .
Column 7, line 61, delete "place din" and insert -- placed in -- .

Signed and Sealed this

Twenty-first Day of July, 1992

Attest:

DOUGLAS B. COMER

*Attesting Officer*   *Acting Commissioner of Patents and Trademarks*